United States Patent [19]

Naveh et al.

US005451662A

[11] Patent Number: 5,451,662

[45] Date of Patent: Sep. 19, 1995

[54] METHOD OF PURIFYING PROTEIN

[75] Inventors: David Naveh, Leiden, Netherlands; John C. Tang, Livingston, N.J.

[73] Assignee: Schering Corporation, Kenilworth, N.J.

[21] Appl. No.: 105,994

[22] Filed: Aug. 12, 1993

Related U.S. Application Data

[63] Continuation of Ser. No. 490,607, Apr. 20, 1990, abandoned, which is a continuation-in-part of Ser. No. 111,886, Oct. 23, 1987, abandoned.

[51] Int. Cl.⁶ .................... C07K 1/18; C07K 14/535
[52] U.S. Cl. ........................... 530/351; 530/416
[58] Field of Search ............. 530/344, 350, 351, 393, 530/399, 412, 416, 417; 435/183, 192, 215

[56] References Cited

U.S. PATENT DOCUMENTS

| | | | |
|---|---|---|---|
| 4,100,149 | 7/1978 | Meiller et al. | 526/46 |
| 4,228,154 | 10/1980 | Fisher et al. | 426/101 |
| 4,438,032 | 3/1984 | Golde et al. | 260/112 R |
| 4,626,355 | 12/1986 | Joustra et al. | 436/161 |
| 4,658,018 | 4/1987 | Urdal et al. | 530/351 |
| 4,736,020 | 4/1988 | Hillen et al. | 530/416 |
| 4,765,903 | 8/1988 | D'Ardrea et al. | 530/351 |
| 4,798,886 | 1/1989 | Kato et al. | 530/416 |
| 5,179,196 | 1/1993 | Johnson et al. | 530/416 |
| 5,256,769 | 10/1993 | Kato et al. | 530/351 |

FOREIGN PATENT DOCUMENTS

| | | | |
|---|---|---|---|
| 0176299 | 4/1986 | European Pat. Off. | C07K 3/16 |
| 0254399 | 5/1986 | European Pat. Off. | C12P 21/02 |
| 52-57200 | 5/1977 | Japan . | |
| 61-120058 | 6/1986 | Japan . | |

OTHER PUBLICATIONS

Methods In Enzymology, vol. V, published 1962 by Academic Press (N.Y.), pp. 3–27.
Cantrell et al., Proc. Natl. Acad. Sci. USA 82:6250 (1985).
Le Technoscope de Biofutur, No. 12, (Jul.–Aug. 1987), pp. 4 and 6.
Pharmacia, "FPLC Ion Exchange and Chromatofocusing," 1985, pp. 62–65 and 88.
Sassenfeld et al., Bio/Technology 2:76 (1984).
Wingfield et al., Journal of Chromotography, 387, 291–300 (1987).
Hockhauser, High Technology, 55–60, (Feb. 1983).
Libby, et al., DNA, 6(3), 221–229 (Jun. 1987).
Wong, et al., Science, 228, 810–815 (1985).
Sparrow, et al., Proc. Natl. Acad. Sci., 82 (1985), 292–296.
Miyajama et al. EMBO Journal, 5, 1193–1197 (1986).
Marston, Biochem. J. 240, 1–12 (1986).
Gillis et al., Immunological Review 63, 166–209 (1982).
Stryer, Biochemistry, second addition, p. 19 (1981), W. H. Freeman & Co. New York, USA.
Fagerstam et al., J. Chromatography, 266, 523–532 (1983).

(List continued on next page.)

*Primary Examiner*—Jeffrey E. Russel
*Attorney, Agent, or Firm*—James M. Gould; Norman C. Dulak

[57] ABSTRACT

An ion-exchange chromatography technique for purifying crude proteins containing closely related impurities, wherein the isoelectric points of the desired protein and the impurities are determined, is disclosed. In performing this technique, the pH for the ion-exchange chromatography is adjusted to a point between the ranges of isoelectric points of the protein fractions to be separated whereby, upon contacting the crude protein mixture at such pH with an ion exchange resin, the proteins in the first and second fractions are oppositely charged and only one of the fractions binds to the ion exchange resin. The application of the technique to the purification of GM-CSF using cation exchange resin is also disclosed.

14 Claims, No Drawings

OTHER PUBLICATIONS

Uruskizaki et al, Biochemicia et Biophysica Acta, 243, 187–192 (1971).
Sluyterman et al, J. Chromatography, 206, 441–447 (1981).
Rabilloud, J. Chromatography, 402, 105–113 (1987).
Regnier, Science, 238, 319–323 (1987).
Gasson et al, Science, 226, 1339–1342 (1980).
Righetti et al, Journal of Chromatography, 220, 115–194 (1981).
Gill, Electrophoresis, 6, 282–286 (1985).
Frey, et al., Electrophoresis, 3 27–32 (1982).
Gemeiner et al, Electrophoresis, 3, 146–151 (1982).
Yost et al., Practical Liquid Chromatography—An Introduction (Perkin–Elmer, U.S.A.) pp. 109–116 (1980).
"Seikaguku Koza 1, Tanpakushitsu no Kagaku I, Burn-riseisei (A Laboratory Manual for Biochemistry 1, Chemistry of Proteins I, Separation and Purification", Ed. Nippon Seikagakukai (Japanese Association of Biochemistry), Pub. Tokyo Kagaku Dojin (published on Mar. 22, 1976), pp. 111–133 (and translation thereof).

METHOD OF PURIFYING PROTEIN

The present application is a continuation application of U.S. application Ser. No. 07/490,607, filed Apr. 20, 1990, now abandoned, which in turn is the United States national application corresponding to International Application No. PCT/US88/03589, filed Oct. 19, 1988 and designating the United States, which PCT application is in turn a continuation-in-part of U.S. application Ser. No. 07/111,886, filed Oct. 23, 1987, now abandoned, the benefit of which applications is claimed pursuant to the provisions of 35 U.S.C. §§120, 363 and 365(C).

BACKGROUND

Ion-exchange chromatography is a conventional chromatographic technique, inherently mild, low cost, large capacity and readily scalable. However, to date it has not been a useful technique for separating closely related impurities from proteins, especially rDNA proteins.

An example of such an rDNA protein is human recombinant GM-CSF. Complementary DNAs (cDNAs) for GM-CSF, factors which support growth and development of granulocytes and macrophages in the blood, have recently been cloned and sequenced by a number of laboratories. Moreover, non-recombinant GM-CSF has been purified from culture supernatants of the Mo cell line (described in U.S. Pat. No. 4,438,032), and the first sixteen amino acids from the N-terminus have been sequenced, Gasson et al., *Science*, Vol. 226, pgs. 1339–1342 (1984). Among the human GM-CSFs, nucleotide sequence and amino acid sequence heterogeneity have been observed. For example, at the amino acid level both threonine and isoleucine have been observed at position 100 with respect to the N-terminal alanine, suggesting that several allelic forms, or polymorphs, of GM-CSF may exist within human populations.

A variety of methods are now available for de novo preparation and cloning of cDNAs, such as cDNAs for GM-CSF, and for the construction of cDNA libraries. By way of example, total mRNA is extracted from cells (e.g., a nontransformed human T cell source) producing polypeptides exhibiting the desired activity. The double-stranded cDNAs can be constructed from this total mRNA by using primer-initiated reverse transcription to make first the complement of each mRNA sequence, and then by priming for second strand synthesis. Subsequently, the cDNAs can be cloned by joining them to suitable plasmid or bacteriophage vectors through complementary homopolymeric tails or cohesive ends created with linker segments containing appropriate restriction sites and then transforming a suitable host. A wide range of expression systems ( i.e., host-expression vector combinations) can be used to produce the proteins purified by the process of this invention. Possible types of host cells include, but are not limited to, bacterial, yeast, insect, mammalian and the like.

Various methods have been disclosed for extracting the GM-CSF from the host cells and subsequently purifying it, but GM-CSF is not always adequately purified in good yield and with retention of biological activity.

SUMMARY OF THE INVENTION

The present invention is directed at a method for separating a crude protein into a relatively pure protein fraction and an impure protein fraction characterized by contacting the crude protein with an ion exchange resin at a pH such that the pure protein and the impurity are oppositely charged, whereby one of the fractions is selectively bound to the ion exchange resin. The ion exchange resin preferably is a strong ion exchange resin and the pure protein fraction preferably is bound to the ion exchange resin. The fraction bound to the ion exchange resin preferably is eluted.

The pH of the crude protein preferably is adjusted to a pH within the range of isoelectric points of the protein fractions to be separated such that there is an amplified net charge difference between the fractions.

The present invention also is directed at a method for determining the pH at which to separate a crude protein into a relatively pure protein fraction and an impure protein fraction characterized by determining the isoelectric points of the pure protein to be recovered and the impurity to be removed and determining the pH within the range of isoelectric points such that the pure protein and the impurity are oppositely charged and an amplified difference between said charges exists. The isoelectric points of the protein fractions preferably are determined by computer simulation or by using isoelectric focusing gels.

The above-described method is useful for the purification of rDNA protein, particularly granulocyte macrophage colony stimulating factor (GM-CSF), more particularly for purifying GM-CSF by separating it from Δ4 GM-CSF.

In a particularly preferred method, protein is purified by sequentially contacting the protein with:
A. an anion exchange resin such as a quarternary amine resin preferably attached to a cross-linked dextran, cellulose, agarose or acrylic support;
B. a cation exchange resin preferably having a sulfonate functionality attached to a cross-linked dextran, cellulose, agarose or acrylic support; and
C. a gel filtration means preferably having a fractionation range of about 5,000 to about 100,000 daltons for proteins.

DETAILED DESCRIPTION

The present invention relates to a high resolution ion-exchange chromatographic separation techique for purifying crude proteins, particularly crude rDNA proteins. In this technique, chromatography is carried out near the isoelectric points of the pure protein sought to be recovered and the impurity sought to be removed, preferably at a pH where an amplified (e.g. the maximum) difference between charges on the pure protein and impurity exists, and where the molecules are oppositely charged (polarized). This amplified net charge difference, which occurs only near the isoelectric point, can be used to select appropriate ion exchange chromatography conditions, resulting in selective binding to ion exchange resin in the near absence of charges. For convenience, this technique is hereafter referred to as Delta Isoelectric Point (DIP) chromatography.

rDNA impurities closely related to a desired rDNA protein are difficult to remove from crude protein by gel filtration chromatography, ion exchange chromatography, hydrophobic interaction chromatography, reversed-phase high performance liquid chromatography, metal chelating affinity chromatography as well as other conventional types of chromatography. These closely related impurities usually are proteins with a molecular weight and charge distribution close to the protein product of interest, usually missing one (or more) charged amino acids. Examples are impurities that are proteolytic degradation products formed by nicking a peptide terminus that is accessible to proteolysis as well as to chromatographic interaction. Such impurities are considered inseparable by conventional ion exchange chromatography.

The DIP chromatography technique differs from conventional ion exchange chromatography in a number of ways. DIP is performed at a pH where proteins to be separated possess very small net electrical charges. This is achieved by loading the ion exchange resin at a pH that is only fractional pH units away from the isoelectric point (pI) of the desired protein and its closely related impurities. This is in contrast to conventional ion exchange chromatography, which is performed at pH's where proteins of interest possess strong electrical charges, and wherein loading is carried out about 1-2 whole pH units away from the pI, an order of magnitude greater than in DIP chromatography.

The pH at which to perform DIP is predicted by computer simulations of charge density vs. pH for the protein and related impurities, or by analytical techniques such as the use of isoelectric focusing gels. In conventional ion exchange chromatography, loading pH is determined by gross net charge on the desired protein, and loading conditions are optimized empirically, if at all. Tedious trial and error experimentation is needed to determine solution conditions.

Unlike conventional ion exchange chromatography wherein no attempt is made to polarize the impurities relative to the desired protein, in DIP chromatography the loading pH is selected so that it lies between the pI of the closely related impurity and that of the desired protein, and therefore, the desired protein attains an opposite electrical charge to the polarized impurity.

For DIP chromatography, a high ionic strength environment is imposed to reduce protein-protein interactions during loading, and a strong ion exchanger is used. In conventional ion exchange technology, to obtain maximum resolution, weak ion exchange resins with lower ionic strength loading conditions are preferred. The low protein-protein interaction during loading in DIP chromatography results in highly selective binding and extremely fine resolution during the loading phase, and additional separation is attained during normal gradient elution. In conventional ion exchange chromatography, non-selective binding occurs during loading and therefore only group separation is achieved during loading; most of the separation is obtained during the elution phase, under strong protein-protein interactions resulting from high locally bound protein densities on the solid matrix.

Computer simulation of charge density vs. pH can be conducted using commercially available software and an appropriate computer (e.g. mainframe, microcomputer or personal computer). For example, a VAX computer (Digital Corp.) may be used with a software package such as "Polypeptide Analysis System" by Intellegentics, Inc., copyright 1981, 1982, 1983, 1984, 1985 and 1986. Using this software the primary amino acid sequence is the input and the charge density distribution can be obtained at different pH's. Alternatively, pI may be determined by using isoelectric focusing (IEF) gel electrophoresis according to procedures well known to those skilled in the art.

DIP chromatography can be applied to proteins, especially recombinant proteins, which have isoelectric points in a pH range wherein the protein is not denatured. The isoelectric points of many proteins are known. For example, see the extensive review article by Righetti, et. al., "Isoelectric Points and Molecular Weights of Proteins—A New Table", in *J. Chrom.*, 220 (1981), pg. 115–194 (*Chromatography Reviews*). Examples of therapeutically significant proteins that exhibit isoelectric point allotropism for which DIP chromatography may be suitable are GM-CSF, leukocyte and lymphoblastoid interferons, growth hormone, superoxide dismutase and erythropoietin. Other proteins include antithrombin III, lactogen, plasminogen, prolactin, urokinase and vitamin $B_{12}$-binding protein.

An example of the application of DIP chromatography is the following procedure for the purification of human recombinant GM-CSF. A particularly difficult aspect of the purification of GM-CSF is the removal of a GM-CSF degradation product missing four N-terminal amino acids and known as Delta 4 ($\Delta 4$). GM-CSF is usually purified by a combination of anion exchange on a quaternary aminoethyl column, gel filtration and reversed phase chromatography, which procedure is not effective in removing the $\Delta 4$ impurity.

DIP chromatography, however, has been successful in removing the $\Delta 4$ impurity. First, a computer simulation of the intact GM-CSF protein was compared to the computer simulation of the $\Delta 4$ impurity, and it was determined that the pI of GM-CSF is 5.24 and the pI of the $\Delta 4$ impurity is 4.98. Next, a working pH within this range had to be determined at which (a) GM-CSF attained an opposite charge to the $\Delta 4$ impurity, and (b) the relative magnitude of the difference between the charges is sufficiently amplified to enable separation. A minute charge difference of 1 charge/molecule (1 ch/mol) between the intact GM-CSF and the $\Delta 4$ impurity exists over a broad pH range (i.e., at pH 0.5, the respective charges are $+16$ and $+15$ and at a pH 11.5, the charges are $-11.1$ and $-12$). However, as predicted by the computer model, close to pH 5 the charge difference between intact GM-CSF and the $\Delta 4$ impurity is amplified (i.e. the relative charge difference is increased) and the molecules are polarized: at pH 5, GM-CSF has $+0.9$ ch/mol, while the $\Delta 4$ impurity possesses only $-0.1$ ch/mol. Hence, the two necessary conditions for DIP are satisfied: charge polarization and amplification.

To further enhance the separation of intact GM-CSF from remaining low pI impurities of the E. coli host cells and from proteolytic destablizing factors, high ionic strength was employed during loading. This diminishes electrostatic interactions among the molecules. Under these high ionic strength conditions, a strong cation exchanger at pH 5, e.g. a column such as a sulfonate functionality attached to a cross-linked dextran, cellulose, agerose or acrylic support (e.g., S-Sepharose, manufactured by Pharmacia, Inc., Piscataway, N.J.) is therefore preferred.

The use of such a cation exchange resin column was found to accomplish a one-step removal of the undesirable $\Delta 4$ impurity, various low pI impurities, a 20 K S. coli impurity not previously removed by other procedures, and a proteolytic factor, thereby stabilizing the final product. Performing the cation exchange chromatography raises the purity of the GM-CSF from about 50% to about 90%, with yields of 70-80%. When followed by a gel filtration step, the purity of the GM-CSF is raised to about 99%.

Following is a general description of a procedure for the isolation and purification of GM-CSF. The action exchange chromatography, preferably on a quaternary aminoethyl column, is a conventional step in the purification of GM-CSF and is performed to remove high pI impurities from the supernatant after the host cells are killed. The gel filtration step, also conventional, is performed to remove high and low molecular weight impurities. While the following describes a process in which the purified protein fraction is bound to the strong ion exchange resin, it is also contemplated that in certain embodiments of the invention the impure protein fraction may be bound to the strong ion exchange resin. Similarly, while the description and example are directed at the continuous passing of the crude protein through an ion exchange resin column, other contacting methods, such as batch contacting, also are contemplated.

General comments: Operations are performed at 2°–15° C. unless otherwise indicated. Protein concentration is determined at each stage by a Coomassie Blue binding assay. If the expected degree of purification is not achieved in any chromatographic procedure, eluted fractions may be re-chromatographed on the same column, or, alternatively, recycled through a previous step or a previous series of steps. This reprocessing can be done on eluted side fractions from a batch or a pool of batches. At any step, concentration may be performed by an ammonium sulfate precipitation, isoelectric point precipitation and/or ultrafiltration. Buffer solutions are made with deionized water (DI), reverse osmosis water (RO), or water for injection (WFI).

STAGE I: CHROMATOGRAPHY ON QUATERNARY AMINE COLUMN

The pH of the crude extract of GM-CSF is adjusted to 5–7.5 with buffer such as 1M Bis-tris (bis[2-hydroxyethyl]imino-tris-[hydroxymethyl]methane) and/or 4N HCl. The solution is then clarified by centrifugation and/or filtration. The conductivity is adjusted to below 10 millisiemens/centimeter (mS/cm) by dilution with water or addition of a salt solution such as 4N NaCl. The batch is applied to a quaternary amine column (i.e., a quaternary amine functionality attached to a cross-linked dextran, cellulose, agarose or acrylic support, such as Q-Sepharose, manufactured by Pharmacia, Inc.) at a loading of not greater than 50 grams of protein per liter of gel. Elution is performed with a gradient in the range of 0–0.4M NaCl or other appropriate salt in a buffer such as 20 mM Bis-tris. Appropriate fractions are combined for further processing.

STAGE II: CHROMATOGRAPHY ON SULFONATE COLUMN

The combined fractions are adjusted to pH 5, which is within the range of isoelectric points of the protein fractions as determined by DIP chromatography, with an acid such as 1M acetic acid or 4N HCl or a base such as 6N NaOH. The conductivity is adjusted to 13 mS/cm with a buffer such as 0.01M acetic acid adjusted to pH 5 with NaOH. The solution is filtered through a 0.2 micron filter and charged onto a sulfonate column (i.e., a sulfonate functionality attached to a cross-linked dextran, cellulose, agarose or acrylic support, such as S-Sepharose) at a loading of not greater than 20 grams of protein per liter of column material. Elution is performed with a solution of a salt such as NaCl at a concentration gradient up to 0.5M in a buffer such as 20 mM acetic acid, 0.13M NaCl, pH 5.0 buffer. Appropriate fractions are combined for further processing. This chromatography step is typically repeated.

STAGE III: AMMONIUM SULFATE PRECIPITATION

Ammonium sulfate is added to the combined S-Sepharose fractions to a final concentration of 50% to 60% saturation. The precipitate is collected by centrifugation. The precipitate may be stored under refrigeration.

STAGE IV: GEL FILTRATION CHROMATOGRAPHY

The ammonium sulfate precipitate is dissolved in a buffer such as 10 mM sodium phosphate, 50 mM citric acid, pH 6 buffer containing up to 0.35M of a salt such as sodium chloride. The solution is centrifuged and filtered through a 0.2 micron range filter prior to loading on to a gel filtration column having a fractionation range of from about 5,000 to about 100,000 daltons for proteins, e.g., Sephacryl S-200 HR (manufactured by Pharmacia, Inc.), pre-equilibrated with the same buffer. The loading is not greater than 3.5 grams of protein per liter of gel. The column is eluted with the same buffer and appropriate fractions are combined. The fractions are dialyzed against a buffer such as an 10 mM phosphate, 2 mM citrate, pH 7.2 buffer. Alternatively, the entire Stage IV can be performed in this latter buffer.

STAGE V: PURIFIED BULK GM-CSF

The combined fractions are filtered through a 0.2 micron or smaller pore size filter and stored at −20° C. or below.

Typical IEF gel electrophoresis procedures are disclosed in the following references:
1. ELECTROPHORETIC TECHNIQUES, Academic Press, (1983) Ed: G. F. Simpson a M. Whittaker "Recent Developments in Isoelectric-focusing" J. S. Fawcett, p. 57
2. ISOELECTRIC-FOCUSING: Theory, Methodology and Application P. G. Righetti, Elsevier Biomedical Press, (1983) p. 148
3. APPLICATION OF SEPARATOR ISOELECTRIC-FOCUSING WITHIN pH RANGE 4–6, P. Gill, Electrophoresis 6:282 (1985)
4. RAPID STAINING OF PROTEINS IN ULTRA THIN ISOELECTRIC FOCUSING IN POLYACRYLAMIDE GEL, M. D. Frey, Electrophoresis 3:27–32 (1982)
5. ULTRA THIN LAYER ISOELECTRIC-FOCUSING OF ENZYMES IN LIVER SAMPLES OF WAGTAILS, M. Germeiner, Electrophoresis 3:146 (1982)

Below is presented an example illustrating procedures for purifying GM-CSF based on the DIP technique.

EXAMPLE 1

PURIFICATION OF GM-CSF

Step 1: Quaternary Amine Column Chromatography

The pH of 180 L of crude GM-CSF extract was adjusted to pH 6.0 with 3.6 L 1M Bis-tris buffer (pH 6.0) and with 2.0 L of 4N HCl. The solution was clarified by centrifugation using a Sharples centrifuge at a feed rate of 0.75 L/min. The supernatant was diluted approximately 1.55 fold with cold deionized water to reach a final conductivity of 5.5 mS/cm. A 12 L column of Q-Sepharose was equilibrated with 10 column volumes of 20 mM Bis-tris buffer at pH 6.0, and 43.6 L of extract was applied to the column at a loading of 20 mg protein per ml of resin. The column (diameter 25 cm) was washed at a flow rate of 250 ml/min. with 120 L of equilibration buffer. A linear gradient was established between 78 L of 20 mM Bis-tris buffer containing 0.03 NaCl at pH 6.0 and 78 L of 20 mM Bis-tris buffer at pH 6.0 containing 0.32M NaCl. Fractions (1.2 L each) were combined based on gel electrophoresis (SDS-PAGE) and the pooled protein (4.9 L) was chromatographed in Step 2.

Step 2: Sulfonate Column Chromatography

The combined fractions (4.9 L) from Step 1 were adjusted to pH 5 with 49 ml 1M acetic acid (pH 5.0) and the conductivity was adjusted to 15 mS/cm with 2 L 0.01M acetic acid adjusted to pH 5 with NaOH. The solution was filtered through a 0.2 micron filter and then charged to a 0.8 L S-Sepharose column previously equilibrated with 20 mM acetic acid containing 0.13M NaCl at pH 5 at a loading rate of 4.7 mg/ml column material. The column was washed with 2.4 L equilibrating buffer, then eluted with a linear gradient established between 5.6 L 20 mM acetic acid at pH 5 containing 0.13M NaCl and 5.6 L 20 mM acetic acid at pH 5 containing 0.5M NaCl. The fractions were combined based on gel electrophoresis. This chromatography step was repeated.

Step 3: Ammonium Sulfate Precipitation

Ammonium sulfate was added to the combined fractions from Step 2 (240 L), giving a concentration of 351 g/L (55% saturation). The solution was held at 4° C. without mixing for 2 hours, then was centrifuged at 4,500 rpm for 30 min at 4° C. to obtain the precipitate.

Step 4: Gel Filtration Chromatography

The ammonium sulfate pellet was dissolved in 36 ml of 18 mM sodium phosphate, 2 mM citric acid, pH 7.2 buffer. The solution was centrifuged at 4,500 rpm for 30 min. and the supernatant filtered through a 0.2 micron filter. The filtrate was loaded onto a 1.9 L Sephacryl S-200 HR column previously equilibrated with phosphatecitrate pH 7.2 buffer at a loading rate of 0.21 mg/ml gel. The column was eluted with 1.9 L of the same pH 7.2 buffer. Fractions were combined based on protein assay.

Step 5: Filtration

The combined fractions from Step 4 were filtered through a 0.2 micron filter and stored at −20° C.

We claim:

1. A method for separating a crude protein mixture having one or more undesired proteins of unknown isoelectric point into a first protein fraction containing a desired protein and a second protein fraction containing one or more undesired proteins, which method comprises:
   (a) determining the isoelectric points of proteins in the crude protein mixture using computer simulation or isoelectric focusing gels;
   (b) adjusting the pH of the crude protein mixture to a point between the ranges of isoelectric points of the protein fractions to be separated; and
   (c) contacting the crude protein mixture at such pH with an ion exchange resin,
   whereby the proteins in the first and second protein fractions are oppositely charged and only one of the fractions binds to the ion exchange resin.

2. The method of claim 1 in which the fraction containing the desired protein binds to the ion exchange resin.

3. The method of claim 2 in which the fraction bound to the ion exchange resin is subsequently eluted.

4. The method of claim 3 in which the desired protein is a recombinant protein.

5. The method of claim 4 in which the desired protein is GM-CSF.

6. The method of claim 4 in which the first protein fraction is bound to an anion exchange resin, eluted and then subjected to gel filtration column chromatography.

7. The method of claim 5 in which the first protein fraction is bound to an anion exchange resin, eluted and then subjected to gel filtration column chromatography.

8. The method of claim 1 in which the desired protein is a recombinant protein.

9. The method of claim 2 in which the desired protein is a recombinant protein.

10. The method of claim 1 in which the ion exchange resin is a strong ion exchange resin.

11. A method for separating a desired protein from a closely related protein impurity of unknown isoelectric point in a crude protein mixture, which method comprises:
    (a) determining the isoelectric points of the desired protein and the impurity using computer simulation or isoelectric focusing gels;
    (b) adjusting the pH of the crude protein mixture to a point between the isoelectric points of the desired protein and the impurity; and
    (c) contacting the crude protein mixture at such pH with an ion exchange resin,
    whereby the desired protein and the impurity are oppositely charged and only one binds to the ion exchange resin.

12. The method of claim 11 in which the desired protein is GM-CSF and the impurity is the $\Delta 4$ impurity.

13. The method of claim 12 in which the pH of the crude protein mixture is adjusted to pH 5.

14. The method of claim 11 in which the ion exchange resin is a strong ion exchange resin.

* * * * *